ID [19]

United States Patent

Higa et al.

[11] Patent Number: 4,882,445

[45] Date of Patent: Nov. 21, 1989

[54] ANTITUMOR CYCLOHEXANONE COMPOSITIONS AND DERIVATIVES THEREOF

[75] Inventors: Tatsuo Higa, Okinawa, Japan; Paul J. Scheuer, Honolulu, Hi.

[73] Assignee: Harbor Branch Oceanographic Institution, Inc., Ft. Pierce, Fla.

[21] Appl. No.: 139,773

[22] Filed: Dec. 30, 1987

Related U.S. Application Data

[63] Continuation of Ser. No. 817,136, Jan. 8, 1986, abandoned.

[51] Int. Cl.$^4$ ........................................... C07D 303/00
[52] U.S. Cl. ...................................... 549/546; 560/231
[58] Field of Search ........................ 549/546; 560/231

[56] References Cited

PUBLICATIONS

M. W. Miller, Tetrahedron, vol. 24 (1968), pp. 4839–4851.
W. D. Lee et al., The Journal of Antibiotics, vol. XXXVII(10), Oct. 1984, pp. 1149–1152.
G. C. S. Reddy et al., The Journal of Antibiotics, vol. XXXVII(12), Dec. 1984, pp. 1596–1599.
Chemical Abstracts 82:111857x and 93:114196u.

*Primary Examiner*—Glennon H. Hollrah
*Attorney, Agent, or Firm*—Carroll F. Palmer

[57] ABSTRACT

This invention relates to antitumor cyclohexanone compositions and derivatives thereof, a process of producing the compositions and a method for inhibiting tumors utilizing the compositions. More particularly, the compositions are cyclohexanone and derivatives thereof which are derived from marine organisms, i.e., the acord worm, Ptychodera sp.

12 Claims, No Drawings

ANTITUMOR CYCLOHEXANONE COMPOSITIONS AND DERIVATIVES THEREOF

CROSS-REFERENCE TO RELATED APPLICATION

This application is a continuation of U.S. Ser. No. 817,136, filed Jan. 8, 1986, now abandoned.

FIELD OF THE INVENTION

This invention relates to new cyclic organic compounds which have useful antitumor activity. More particularly, this invention relates to new cyclohexanone and cyclohexanone derivative antitumor compositions derived from marine organisms, i.e., the acorn worm, Ptychodera sp.

BACKGROIUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the inflinction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Various new six membered ring organic compounds which have been reported to have or potentially have antitumor and antibiotic activity have been isolated from bacteria and mold. Compounds of particular interest are described in the following references: Y-aminoepoxysemiquinone is disclosed by M. D. Lee, et al., "New Antitumor Antibiotic, LL-C10037a Fermentation, Isolation and Structure Determination", *The Journal of Antibiotics*, Vol. 37, No. 10, pp. 1149–1152 (October 1984); 4-amino-7-oxa-bicyclo[4,1,0]hept-3-ene-2,5-dione-3-carboxamide is disclosed by G. C. S. Reddy, et al., "Stereochemistry of the Epoxydon Group Antibiotic G7063-2 Isolated From A *STREPTOMYCES* Species HPL Y-25711", *The Journal of Antibiotics*, Vol. 37, No. 12, pp. 1596–1599 (December 1984); various other compounds are described in M. W. Miller, "The Structure of Terremutin," *Tetrahedron*, Vol. 24, pp. 4839–4851 (1968); and A. Closse, et al., *Helv. Chim. Acta*, Vol. 49, p. 204 (1966). While these references show compounds which may have antibiotic and antitumor application, the need exists for new compounds which display a favorable amount of antitumor activity.

It has now been found that certain six membered ring organic compounds derived from extracts of the acorn worm, Ptychodera sp. possess useful antitumor activity.

SUMMARY OF THE INVENTION

It is therefore an object of the invention to provide novel composition which are useful as antitumor agents and a process for producing such novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formula (I–IV)

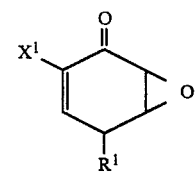

I

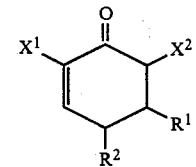

II

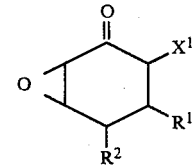

III

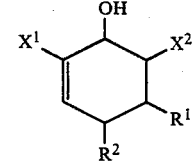

IV wherein $X^1$ and $X^2$ are the same or different and are a halogen, hydroxy, or hydrogen;

$R^1$ and $R^2$ are selected from the group consisting of hydroxy, lower acyloxy and lower alkoxy.

In preferred embodiments of the invention, the composition is substantially pure $X^1$ or $X^2$ is bromine, $R^1$ is a lower acyloxy or alkoxy which has from 1 to 4 carbon atoms. In more preferred embodiments of the invention, the invention comprises compositions of the formulae (V–IX):

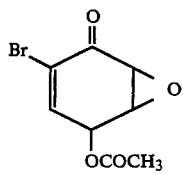

V

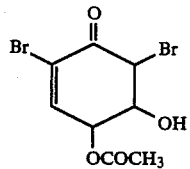

VI

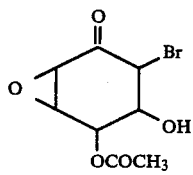

VII

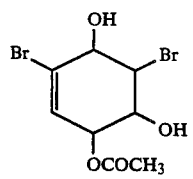

VIII

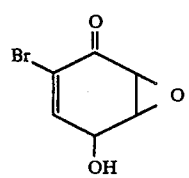

IX

As embodied and fully described herein, the invention also comprises an antitumor composition comprising, as active ingredient, an effective antitumor amount of one or more compositions according to formulae I-IX and a non-toxic pharmaceutically acceptable carrier or diluent.

As embodied and fully described herein, the invention also comprises a process to produce the compounds of formulae I-IX. The process comprises the steps of collecting acorn worm, Ptychodera, sp., contacting the acorn worm with a suitable organic solvent; homogenizing the acorn worm and solvent mixture to obtain a extract thereof; and isolating a compound according to formulae I-X from the extract.

In preferred embodiments of the invention the suitable organic solvent is selected from the group consisting of acetone, methyl ethyl ketone, ethyl acetate, methanol, ethanol, and methyl isobutyl ketone.

As embodied and fully described herein, the invention further comprises a method for inhibiting tumors in a host and a therapeutic method for treating cancerous cachexia comprising contacting a tumor with an effective antitumor amount of one or more compositions of formulae I-IX.

It is to be understood that both the foregoing general and the followig detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formulae (I-IV):

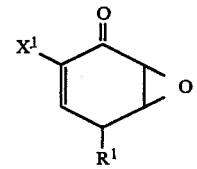

I

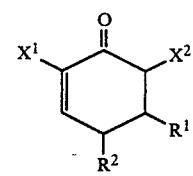

II

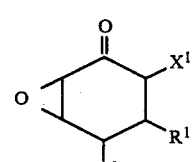

III

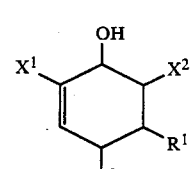

IV wherein $X^1$ and $X^2$ are the same or different and are a halogen, hydroxy, or hydrogen;

$R^1$ and $R^2$ are selected from the group consisting of hydroxy, lower acyloxy and lower alkoxy.

In preferred embodiments of the invention, the composition is substantially pure and $X^1$ or $X^2$ is bromine, $R^1$ is a lower acyloxy or alkoxy having from 1 to 4 carbon atoms. In more preferred embodiments of the invention, the invention comprises compositions of the formulae (V-IX):

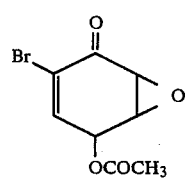

V

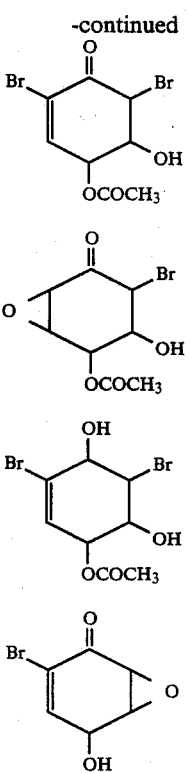

In accordance with the invention, an antitumor composition is provided comprising as active ingredient an effective antitumor amount of one or more of the compositions described above and identified by formulae I-IX in a non-toxic pharmaceutically acceptable carrier or diluent. While effective amounts may vary, as conditions in which the antitumor compositions are used vary, a minimal dosage required for activity in generally between 0.01 and 100 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compositions according to formulae I-IX. The effectiveness of the compositions of the invention for inhibiting tumors indicates their usefulness for controlling tumors in hosts including mammals and for treating cancerous cachexia.

In accordance with the invention, a process to produce a compound according to formulae I-IX comprises the steps of: collecting acorn worm Ptychodera sp.; contacting the collected acorn worm with a suitable organic solvent; homogenizing the solvent and acorn worm mixture to obtain an extract of the solvent; and isolating a compound according to formulae I-IX.

A detailed description and explanation of a preferred embodiment of the process of the invention to produce the compound according to formula I-IX is as follows: acorn worm Ptychodera sp., is collected from submarine caves in the vicinity of Maui, Hawaii. The acorn worm is homogenized with acetone (a first solvent) in a mortar or blender. The acetone extract is concentrated and partitioned between water (a second solvent) and methylene chloride (a third solvent) to give an organic residue. The residue is grossly separated into fractions which yield various compositions. Compositions according to the invention are isolated by various chromatographic techniques from the fractions obtained.

While acetone, water and methylene chloride are the presently preferred choices for the first, second and third solvents, respectively, other suitable solvents may be substituted. A suitable first solvent should be capable of extracting a compound according to any one of formulae I-IX from other components of the acorn worm. Suitable first solvents which may be substituted for acetone include, but are not limited to, the following organic solvents: methyl ethyl ketone; ethyl acetate; methanol; ethanol; and methyl isobutyl ketone. Suitable second and third solvents should be capable of extracting and separating into various fractions the various compounds of formulae I-IX from other components that may be present in the first solvent extract. Suitable second and third solvents which may be substituted for either water or methylene chloride or both include, but are not limited to either water or methylene chloride alone or, the following organic solvents: chloroform; trichloroethylene; hexane, and lower alkanes. Different ratios of first, second and third solvents and any combination may be used in the invention as would be known to those skilled in the art.

Any suitble fractionation and isolation techniques may be utilized in accordance with the process of the invention. Suitable fractionation techniques include various chromotography techniques such as, high pressure liquid chromatography (HPLC) with a suitable column as would be known to those skilled in the art (e.g., a Whatman partisil column (M9 50/10) eluted with a suitable solvent such as, for example, 4:1 to 2:1, hexanes:ethyl acetate.

It is therefore apparent that the compositions of the invention, the process for producing the compositions of the invention and the methods for utilizing the compositions of the invention to inhibit tumors are effective for inhibiting or destroying tumors and therefore controlling diseases caused by or related to such tumors in fulfillment of the objects of the invention.

EXAMPLES

The invention will now be illustrated by examples. The examples are not intended to be limiting of the scope of the present invention. In conjunction with the detailed and general description above; the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

EXAMPLES 1-5

Acorn worm, Ptychodera sp., 294 gms (wet weight with a minor amount of silt) was collected from submarine caves of Maui, Hawaii and was homogenized with acetone in a mortar. The acetone extract (800 ml) was concentrated and partitioned between water and $CH_2Cl_2$, ($3 \times 200$ ml) to give 740 mg of organic residue. The residue was grossly separated on a silica gel (25 g) column (2:1 hexanes-EtOAc) into 15 fractions. Elution volume and yield of each fraction are shown in Table 1.

TABLE 1
Gross Separation of the Extract of *Ptychodera sp.*

| Fr. # | Elution Vol. (ml) | Yield (mg) | Fr. # | Elution Vol. (ml) | Yield (mg) | Fr. # | Elution Vol. (ml) | Yield (mg) |
|---|---|---|---|---|---|---|---|---|
| 1 | 20 | 57 | 6 | 20 | 47 | 11 | 40 | 7.9 |
| 2 | 20 | 121 | 7 | 20 | 35 | 12 | 20 | 2.5 |
| 3 | 20 | 108 | 8 | 20 | 15 | 13 | 40 | 11.2 |
| 4 | 20 | 45 | 9 | 20 | 7.9 | 14 | 40 | 8.6 |
| 5 | 20 | 78 | 10 | 20 | 4.9 | 15 | 300 | 11.4 |

Each of the fractions 1-12 were separated by HPLC with a Whatman Partisil column (M9 50/10) by eluting with 4:1 to 2:1 hexanes:ethylacetate. Yields of major constituents are shown in Table 2.

TABLE 2
Yields of Compounds Isolated from *Ptychodera sp.*

| Compound # | 1 | 2 | 3 | 4 | 5 |
|---|---|---|---|---|---|
| Yield (mg) | 56.2 | 19.0 | 8.5 | 24.1 | 67.6 |

EXAMPLE 1

[4S,5R,6R]-4-Acetoxy-2-bromo-5,6-epoxy-2-cyclohexenone

Preparation of:

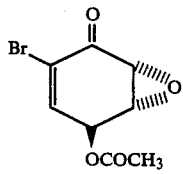
(1)

Compound (1) was obtained from fractions 2-8. Recrystallization of the HPLC-separated sample from hexanes-EtOAc gave colorless needles, mp 93°-94°, $[\alpha]_D^{19}$ +265° (c 0.12, CHCl$_3$,). HRMS m/z 245.9542 (calcd. for C$_8$H$_7$$^{79}$BrO$_4$ 245.9528). EIMS m/z 248 (3.7), 246 (3.9), 206 (25), 204 (25), 190 (3.7), 188 (3.4), 178 (11), 176 (11), 177 (15.4), 175 (15.9), 161 (11.3), 159 (12.8), 133 (12.3), 131 (13.7), 125 (13.2), 107 (10.1), 97 (33.3), and 43 (100%). IR (KBr) 1730, 1700, 1615, 1375, 1240, 1210, 1030, 970, 910, and 780 cm$^{-1}$. $^1$H NMR (CDCl$_3$) δ 7.04 (1H, dd, J=5.3, 2.3 Hz), 5.73 (1H, dt, J=5.3, 1.3 Hz), 3.75 (1H, ddd, J=3.4, 2.3, 1.3 Hz), 3.68 (1H, dd, J=3.4, 1.2 HZ), and 2.13 (3H, s).

EXAMPLE 2

[4S,5R,6S]-4-Acetoxy-2,6-dibromo-5hydroxy-2-cyclohexenone (2)

Preparation of:

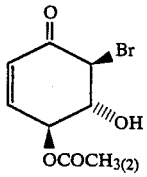
(2)

This compound was contained in fractions 4-12 and was isolated in 19 mg. Purification by HPLC gave 15.1 mg of glass which solidified during storage in a freezer. Recrystallization from hexane-ethyl acetate gave colorless crystals, mp 136°-138°. HRMS m/z 325.8825±0.0326 (calcd for C$_8$H$_8$Br$_2$O$_4$ 325.8789); EIMS m/z 330, 328, 326 (M+), 288, 286, 284 (M—C$_2$H$_2$O), 270, 268, 266 (M—C$_2$H$_2$O —H$_2$O), 249, 247 (M—Br), 231, 229 (M—Br, —H$_2$O), 207, 205 (M—Br, —C$_2$H$_2$O), 206, 204 (M—Br, —C$_2$H$_3$O), 189, 187 (M—Br, —C$_2$H$_2$O —H$_2$O), 164 162, 158, 126, 125, 97, 53, 51, and 43 (base); UV λ$_{max}$(MeOH) 255 (ε 5200); IR (KBr) 3430, 2920, 1725, 1700, 1607, 1218, and 1043 cm$^{-1}$; $^1$H NMR (CDCl$_3$) δ 7.22 (1H, d, J=2.4 Hz), 5.63 (1H, dd, J=8.2, 2.4 Hz), 4.67 (1H, d, J=11.1 Hz), 4.17 (1H, ddd, J=11.1, 8.2, 2.7 Hz), 3.02 (1H, d, J=2.7 Hz, D$_2$O exchangeable), and 2.18 (3H, s); $^{13}$C NMR (CDCl$_3$) δ 146.0, (C-3), 122.7 (C-2), 74.6 (C-4), 72.7 (C-5), 56.7 (C-6), and 20.8 (CH$_3$).

EXAMPLE 3

4-Acetoxy-2-bromo-5,6-epoxy-3-hydroxycyclohexanone(3)

Preparation of:

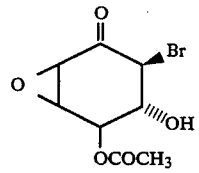
(3)

An additional HPLC purification of the 8.5 mg sample obtained from fractions 4-12 was carried out and gave an oil. $^1$H NMR (CDCl$_3$) δ 5.31 (1H, dd, J=5.1, 2.9 Hz), 4.96 (1H, d, J=2.5 Hz), 4.16 (1H, m), 3.81 (1H, t, 3.1 Hz), 3.56 (1H, d, J=3.6 Hz), 2.62 (1H, d, J=5.5 Hz), and 2.20 (3H, s).

EXAMPLE 4

[3S,4R,5S,6R]-3-Acetoxy-1,5-dibromo-4,6-dihydroxycyclohexene

Preparation of:

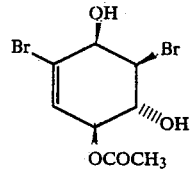
(4)

The compound was contained in fractions 5-12 and isolated as an oil in total 24.1 mg slightly contaminated with other products. Crystallization from 2:1 hexanes-EtOAc gave colorless crystals, mp 150.5°-151.5°. HRMS m/z 232.9628 [M+-H$_2$O, —Br], calcd. for C$_8$H$_8$ $^{81}$BrO$_3$ 232.9636], 205.9590 (calcd. for C$_6$H$_7$ $^{79}$BrO$_3$ 205.9579), and 190.9523 (calcd. for C$_6$H$_6$ $^{81}$BrO$_2$ 190.9531). EIMS m/z 233 (29), 231 (29), 208 (19), 206 (20), 191 (99), 189 (96), 166 (52), 164 (52), 110 (100), 109 (62), 82 (20), 80 (15), and 43 (94). IR (KBr) 3420, 1720, 1365, 1285, 1240, 1105, 1080, 1045, and 1025 cm$^{-1}$. $^1$H NMR (CDCl$_3$), δ 6.10 (1H, d, J=2.7 Hz), 5.27 (1H, dd, J=7.0, 2.7 Hz), 4.47 (1H, dd, J=3.4, 3.3 Hz), 4.25 (1H, dd, J=11.4, 3.3 Hz), 4.17 (1H, dd, J=11.3, 7.1 Hz), 2.77 (1H, d, J=3.7 Hz), 2.64 (1H, bs), and 2.11 (3H, s).

EXAMPLE 5

Preparation of [4S,5R,6R]-4-Acetoxy-2,6-dibromo-5-hydroxy-2-cyclohexenone (5)

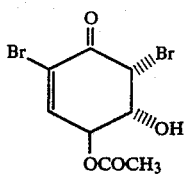

(5)

The compound (5) was most abundant and obtained from fractions 4-12 in total 67.6 mg. A part of the sample was repurified by HPLC to give a glass which solidified during storage in a freezer. An attempt to recrystallize the solid from cyclohexane-benzene was unsuccessful, presumably because of partial epimerization of the compound to compound 2 (above). Optical rotation of the pure sample was recorded as $[\alpha]_D$ 23° +130° (c 0.1, $CH_2Cl_2$). HRMS m/z 325.8823 (calcd for $C_8H_8Br_2O_4$ 325.8789); EIMS m/z 330, 328, 326, 288, 286, 284, 270, 268, 266, 249, 247, 231, 229, 207, 205, 189, 187, 164, 162, 161, 159, 126, 125, 97, 53, 51, and 43 (base); UV $\lambda_{max}$ (MeOH) 256 ($\epsilon$ 5500) and 202 nm ($\epsilon$ 4200); IR (KBr) 3430, 2920, 1720, 1700, 1605, 1370, 1215, 1090, and 1040 $cm^{-1}$; $^1H$ NMR ($CDCl_3$) δ 7.18 (1H, d, J=2.7 Hz), 5.61 (1H, dd, J=7.4, 2.7 Hz), 4.77 (1H, d, J=3.5 Hz), 4.06 (1H, br dd, J=7.4, 3.5 Hz), 2.88 (1H, br s, $D_2O$ exchangeable), and 2.18 (3H, s); $^{13}C$ NMR ($CDCl_3$) δ 145.2 (C-3), 72.7 (C-5), 71.6 (C-4), 52.3 (C-6), and 20.8 ($CH_3$).

ANTITUMOR ACTIVITIES OF THE COMPOUNDS OF THE INVENTION

The following assay method was utilized to illustrate the antitumor effectiveness of the compositions of Formulae I, II, and IV corresponding to compositions 1, 2 and 4 of the examples.

L1210 And P388 MOUSE LEUKEMIA CELL CYTOXICITY ASSAY 24-WELL PLATE SCREENING ASSAY AND TUBE ASSAY PROTOCOL

Materials Utilized

Media—Dulbeccos with glucose and pyruvate (Biologos, Inc) with 10% horse serum, (Biologs, Inc) and 1.0 ug/ml gentamicin (Gibco).

Cells—L1210 and P-388 mouse leukemia cells (American Type Culture Collection) and A549 human lung, HCT-8 human colon and MCF-7 human breast cells in media at a concentration of $5 \times 10^4$ cells/ml. Sterile 24-well culture plates (Nunc) for screening or 12×75 mm glass culture tubes (Becton-Dickinson) for tube assay. Microdispenser with 1 to 5 ul increments (Drummond Scientific Co. Broomall PA).

Finnpipette with 5 to 50 ul increments and Finnpipette with 50 to 200 ul increments.

Procedure

1. Sample of the composition to be assayed is added to each well or tube in an amount of from 200 ug/ml and 100 ug/ml for screening. For DDC of known active compounds use log concentrations from 100 ug/ml to 0.01 ug/ml for range-finding assay; when range has been determined, use five concentrations between highest and lowest active concentrations.

2. Add 2.0 ml of $5 \times 10^4$ cell suspension in media to each well or tube. Tubes are loosely covered with parafilm.

3. Incubate in 5% $CO_2$ incubator 48 hours.

4. Visually read plates with inverted microscope, comparing with solvent control. Assign activity as follows:

0 = 90–100% of control growth
   1+ = 75–89% of control growth
   2+ = 50–74% of control growth
   3+ = 25–49% of control growth
   4+ = 25% of control growth Repeat all positive samples using tube assay.

5. For Tube assays—Mix tube well on vortex and remove 0.5 ml aliquot and add to 9.5 ml nf diluent fluid (Isoton-Coulter) in Accuvette (Coulter) and mix well by inversion immediately before counting, taking care not to produce excessive bubbles. Count on Coulter Counter (Counter is set to count 0.5 ml of the solution; therefore counts may be converted to cll/ml in original assay tube by multiplying count by 40.

Positive Control—Vinblastine or Vincristine in aqueous solution.

Final Conc. of Vinblastine or Vincristine control (use 2 ul/assay)

| Solution Conc. | Amt added | Final conc. in test |
| --- | --- | --- |
| 10 mg/ml | 2 ul | 10 ug/ml |
| 1 mg/ml | 2 ul | 1 ug/ml |
| 0.1 mg/ml | 2 ul | 0.1 ug/ml |
| 0.01 mg/ml | 2 ul | 0.001 ug/ml |

Notes:
For solvents other than water, allow solvent to evaporate from tube or well in hood.

Chloroform and butanol cannot be used in the plastic 24-well plates—use glass tubes.

Always run a solvent control in duplicate in the last two wells of each plate or four tubes for each rack of 72 or less tubes. Also run four wells or tubes with media and cells only per run of plates or tubes. When using volumes of aqueous solutions greater than 200 ul, dry sample and bring up to desired concentration in media.

The results of the above assay are summarized below in Table 3. Compounds of formula I/1; II/2; and IV/4 are cytotoxic in vitro against P-388 murine leukemia cells; L-1210 murine leukemia cells; A549 human lung cells; HCT-8 human colon cells; and MCF-7 human breast cells.

TABLE 3

Antitumor Assay Results

| Compound Formula/Example | Concentration | P388 | L1210 |
| --- | --- | --- | --- |
| I/1 | 100 ug/ml | 3+ | |
| | 10 | 4+ | 4+ |
| | 1 | 3+ | 3+ |
| | 0.1 | 3+ | 2+ |
| | 0.01 | 2+ | 1+ |
| II/2 | 100 | 3+ | |
| | 10 | 3+ | |
| | 1 | 2+ | |
| IV/4 | 100 | 4+ | |
| | 10 | 4+ | |
| | 1 | 3+ | |

| | | A549 | HCT-8 | MCF-7 |
| --- | --- | --- | --- | --- |
| I/1 | 50 ug/ml | 4+ | 4+ | |
| | 20 | 4+ | 4+ | |
| | 10 | 4+ | 4+ | 4+ |
| | 5 | 4+ | 4+ | |

TABLE 3-continued

| Compound Formula/Example | Antitumor Assay Results Concentration | | P388 | L1210 |
|---|---|---|---|---|
| | 1 | ND | 3+ | 3+ |
| | 0.5 | | ND | |
| | 0.1 | | | 2+ |
| | 0.01 | | | ND |
| II/2 | 50 ug/ml | | | ND |
| | 5 | | | ND |
| IV/4 | 50 | | | 4+ |
| | 5 | | | ND |

The scope of the present invention is not limited by the description, examples, and suggested uses herein and modifications can be made without departing from the spirit of the invention. For example, it may be noted that other derivatives of the compounds of examples 1-5 such as a fluorinated derivative may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A compound according to one of the formulae:

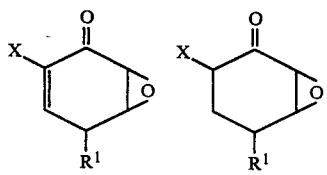

wherein:
X is halogen
$R^1$ is —OH, —OCOR or —OR and
R is 1 to 4 carbon alkyl.

2. A compound according to claim 1 wherein X is bromine.

3. A compound according to claim 1 wherein $R^1$ is acetyl.

4. A compound of the formula:

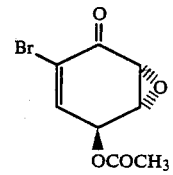

5. A compound according to claim 1 of the formula:

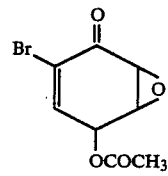

6. A compound according to claim 1 of the formula:

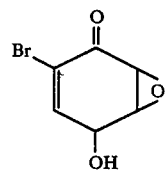

7. A compound according to claim 1 that is substantially pure.

8. A pharmaceutical composition comprising, as an active ingredient, a pharmaceutically effective amount of one or more compounds of claim 1 and a non-toxic pharmaceutically acceptable carrier or diluent.

9. A pharmaceutical composition comprising, as an active ingredient, a pharmaceutically effective amount of the compound of claim 2 and a non-toxic pharmaceutically acceptable carrier or diluent.

10. A pharmaceutical composition comprising, as an active ingredient, a pharmaceutically effective amount of the compound of claim 4 and a non-toxic pharmaceutically acceptable carrier or diluent.

11. A pharmaceutical composition comprising, as an active ingredient, a pharmaceutically effective amount of the compound of claim 5 and a non-toxic pharmaceutically acceptable carrier or diluent.

12. A pharmaceutical composition comprising, as an active ingredient, a pharmaceutically effective amount of the compound of claim 6 and a non-toxic pharmaceutically acceptable carrier or diluent.

* * * * *

UNITED STATES PATENT AND TRADEMARK OFFICE
CERTIFICATE OF CORRECTION

PATENT NO. : 4,882,445

DATED : November 21, 1989

INVENTOR(S) : Tatsuo Higa, Paul J. Scheuer

It is certified that error appears in the above-identified patent and that said Letters Patent is hereby corrected as shown below:

Abstract: line 8: "acord" should read --acorn--.
Column 1: line 33: "inflinction" should read --infliction--.
Column 6: line 26: "suitble" should read --suitable--.
Example 2:

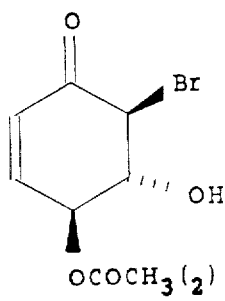 should read 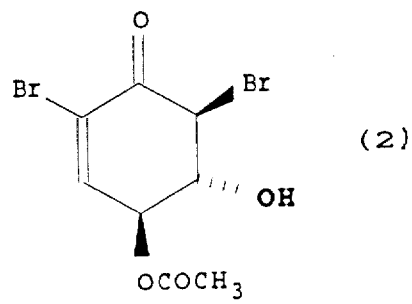

Signed and Sealed this

Ninth Day of July, 1991

Attest:

HARRY F. MANBECK, JR.

Attesting Officer

Commissioner of Patents and Trademarks